United States Patent
Odrich

(10) Patent No.: US 8,640,709 B2
(45) Date of Patent: Feb. 4, 2014

(54) MULTI-PIECE PUNCTAL PLUG

(76) Inventor: Steven Odrich, Bronx, NY (US)

( * ) Notice: Subject to any disclaimer, the term of this patent is extended or adjusted under 35 U.S.C. 154(b) by 0 days.

(21) Appl. No.: 13/478,780

(22) Filed: May 23, 2012

(65) Prior Publication Data

US 2012/0253299 A1 Oct. 4, 2012

Related U.S. Application Data

(63) Continuation of application No. 12/326,622, filed on Dec. 2, 2008, now Pat. No. 8,201,562.

(51) Int. Cl.
*A61B 17/00* (2006.01)

(52) U.S. Cl.
USPC ............................................. 128/887

(58) Field of Classification Search
USPC ................. 128/846, 887, 830, 836, 838, 840; 606/300, 301, 304, 309, 315, 326, 327, 606/191, 194, 198; 24/606, 607; 600/32
See application file for complete search history.

(56) References Cited

U.S. PATENT DOCUMENTS

| | | | | | |
|---|---|---|---|---|---|
| 3,479,075 | A | * | 11/1969 | Swanno | 292/19 |
| 5,469,867 | A | * | 11/1995 | Schmitt | 128/898 |
| 6,016,806 | A | * | 1/2000 | Webb | 128/846 |
| 6,082,362 | A | * | 7/2000 | Webb | 128/846 |
| 6,629,533 | B1 | * | 10/2003 | Webb et al. | 128/887 |
| 6,846,319 | B2 | * | 1/2005 | Ginn et al. | 606/213 |
| 7,647,930 | B2 | * | 1/2010 | Ginn | 128/831 |
| 2006/0020248 | A1 | * | 1/2006 | Prescott | 604/294 |

FOREIGN PATENT DOCUMENTS

EP 720833 A1 * 7/1996 ............. A61B 10/00

* cited by examiner

*Primary Examiner* — Patricia Bianco
*Assistant Examiner* — Raymond E Harris
(74) *Attorney, Agent, or Firm* — Notaro, Michalos & Zaccaria P.C.

(57) ABSTRACT

A multi-piece punctal plug has one a superficial plug removably connected to an anchor plug deeper in the naso-lacrimal canaliculus. The anchor is fixed to the wall of the lacrimal duct while the superficial plug is axially and detachably secured to the anchor plug so that the multi-plug complex may be inserted or removed together as one, or the superficial plug may be detached separately and replaced securely without disturbing the anchor. Removal and insertion is accomplished by a specific tool having an end for reversibly engaging the plugs.

11 Claims, 5 Drawing Sheets

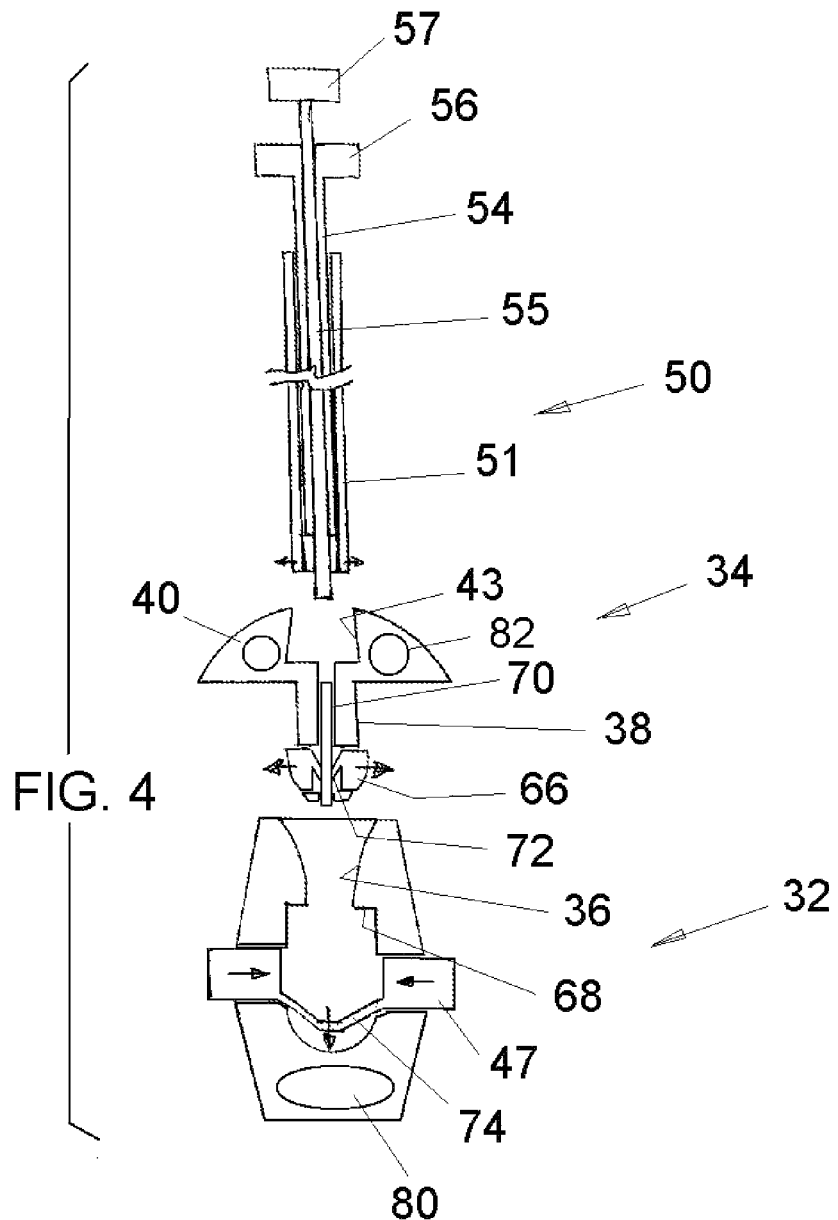

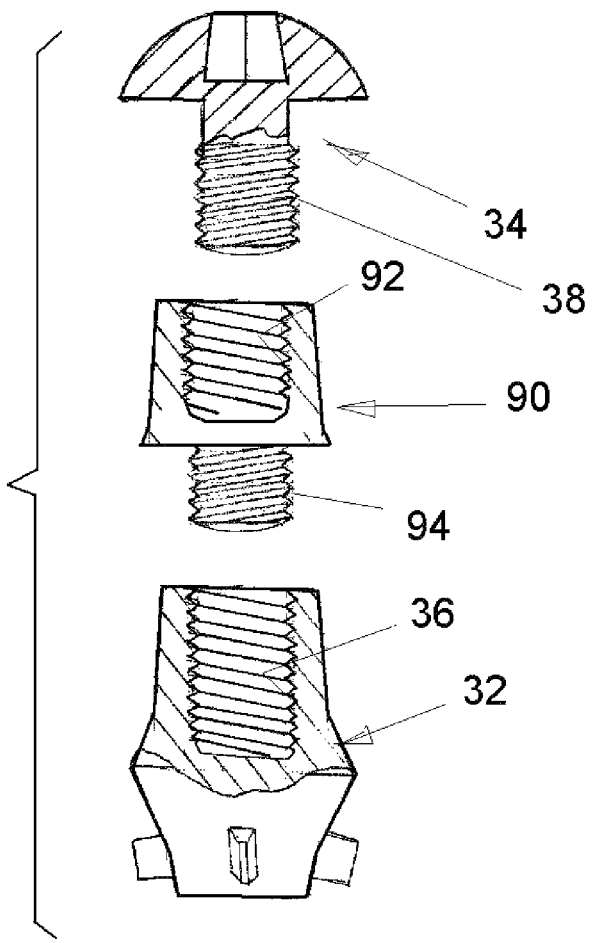

MULTI-PIECE PUNCTAL PLUG

CROSS-REFERENCE TO RELATED APPLICATIONS

This is a continuation of U.S. patent application Ser. No. 12/326,622 filed Dec. 2, 2008, which application is incorporated herein by reference and is now U.S. Pat. No. 8,201,562, issued Jun. 19, 2012.

FIELD AND BACKGROUND OF THE INVENTION

The present invention relates generally to the field of ophthalmology, and in particular to a new and useful punctal plug that is made up of multiple parts to enhance its effectiveness.

US Patent Application 2005/0232972 to the same inventor as the present application, is incorporated here by reference, and discloses a method and an apparatus for administering an active agent to a subject by applying the active agent to at least one surface of an ocular implant such as a punctal plug, and installing the implant, e.g. inserting the punctal plug into a punctal aperture of the subject.

Although the use of punctal plugs to deliver a drug to the eye, or to the body, or for other purposes, is known, retention of the plugs over time continues to be problematic since the plugs tend to fall out prematurely.

SUMMARY OF THE INVENTION

It is accordingly an object of the present invention to overcome the retention problem of current punctal plug delivery designs by providing a multi-piece punctal plug for any appropriate function, that has an anchoring component which is designed to be securely anchored in the lacrimal duct near the punctum, to receive a superficial plug component that, in turn, can be attached securely and detached at the practitioner's discretion, in a controlled fashion.

This may be accomplished, according to the invention, and for example, by threading the superficial plug component to the anchoring component for a "screw in" and "unscrew" technique, or a mechanical spring loaded latching structure and process may be used, or a bayonet connection, or other reversible and controllable attachment mechanism and method that is currently known or that is here after discovered, may be used.

The invention is directed to the punctal plug in general and may be embodied, for example as follows.

1. A punctal plug of multi-piece design, specifically with an anchoring piece which sits deep within the canaliculus and is firmly attached to the walls using any method, e.g. a mechanical method with an expansile element to wedge the anchoring plug permanently in position, spring loaded prongs which emerge from the anchoring plug and fix it in position reversibly, or a chemical method which bonds it in place.

2. A punctal plug of multi-piece design with a superficial part which is designed to attach, reversibly, to the deeper anchoring plug. Two possible but not limiting embodiments are using a screw-in method or a spring-loaded latching method as noted above, both enabling the removal of the superficial plug at the practitioner's discretion, while leaving the anchoring plug in place deeper in the canal.

3. A punctal plug of multi-piece design in which the anchoring plug is designed to receive the superficial plug or plugs. This might include a screw in opening or a shape to receive a spring-loaded latch.

4. A punctal plug of multi-piece design wherein either or all parts are imparted with medicine to deliver to the eye or the systemic circulation.

5. A punctal plug of multi-piece design in which all pieces are possessed of a radio-opaque element which allows for identification on X-ray/imaging procedures.

The invention includes the method for unscrewing or otherwise disconnecting the superficial plug component from the anchoring plug or anchor component, as this has not been described previously.

Accordingly, a further object of the invention is to provide a punctal plug that comprises an anchor for being received in a lacrimal duct and a plug for extending into the anchor, the anchor being fixed to the wall of the lacrimal duct and the plug being axially and detachably secured to the anchor so that with the plug connected to the anchor, the plug and anchor can be inserted into, and removed from the lacrimal duct using a tool having an end for engaging the plug.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4 is a view similar to FIG. 2 but of a further embodiment of the invention; and FIG. 5 is a view similar to FIG. 2 but of a still further embodiment of the invention.

DESCRIPTION OF THE PREFERRED EMBODIMENTS

Figure 1:
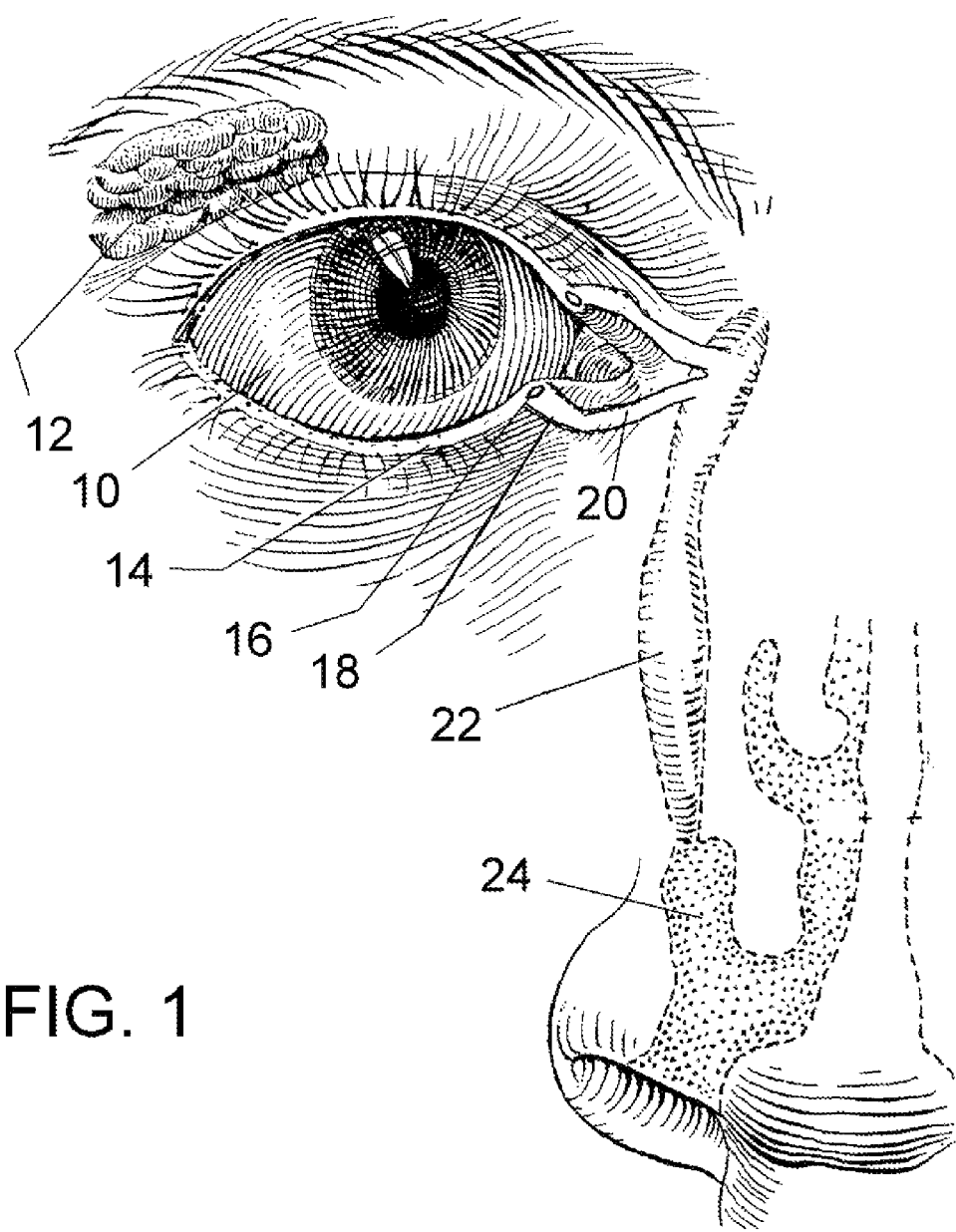
FIG. 1 is a partial and schematic view of the eye and nose area of a patient who would benefit from the punctal plug arrangement of the present invention.

Referring now to the drawings, in which like reference numerals are used to refer to the same or similar elements, FIG. 1 shows the eye and nose area of a patient who would benefit from the punctal plug arrangement of the present invention. To better understand the environment in which the invention will operate, the patient is shown to have an eye 10 above which are located lacrimal glands 12 for producing tears. The tears will wet and coat the eye and will eventually move to the upper and lower lid margins 14 and then be channeled to the upper and lower punctum 16. The tears will then travel along the upper and lower canaliculus 18 and lacrimal ducts 20 (collectively referred to here simply as the lacrimal ducts), into the nasolacrimal duct 22 and then to the nasal cavity 24.

Figure 2:
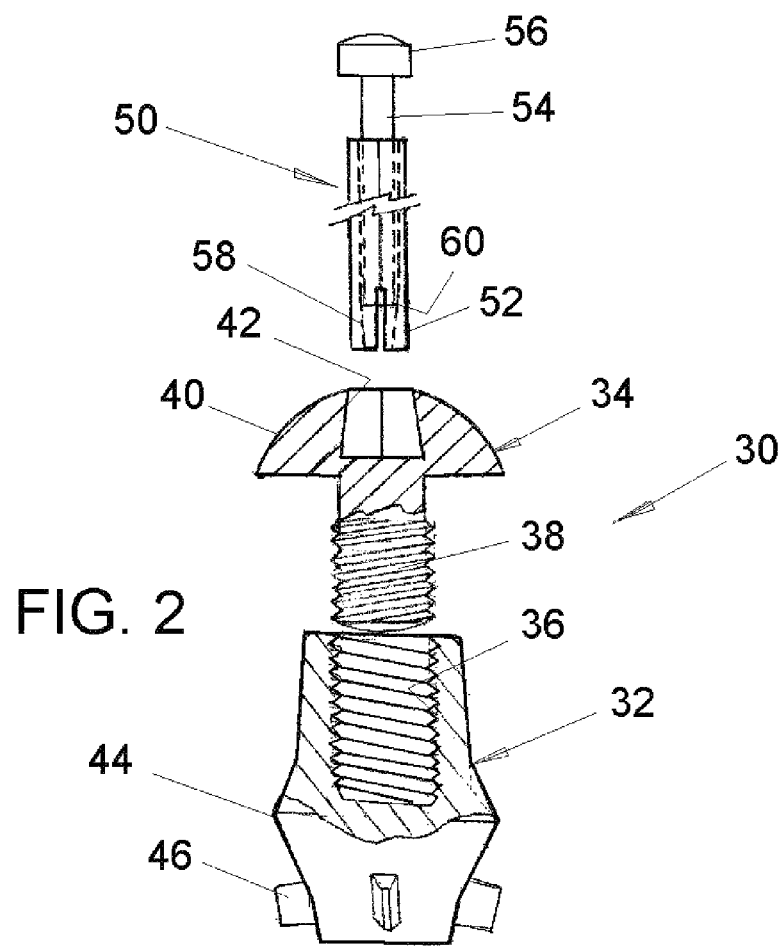
FIG. 2 is an enlarged exploded view that is partly in section, of an embodiment of the invention.
Figure 3:
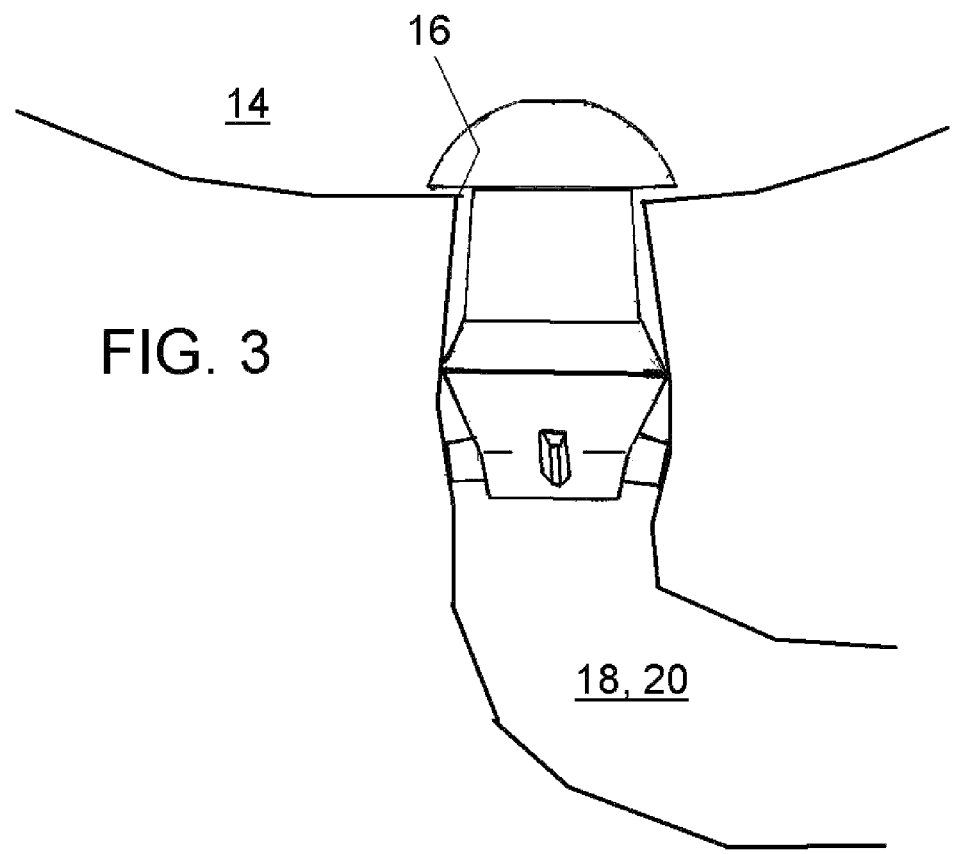
FIG. 3 is a view of the embodiment of FIG. 2 in the lacrimal duct of a patient.

Referring now to FIGS. 2 and 3, a punctal plug arrangement 30 of the present invention is received in one of the lacrimal ducts 18, 20, at or near the corresponding lacrimal punctum 16 of a patient. Since the patient has four such lacrimal ducts, up to four punctal plugs of the present invention can be used, each for a known mechanical purpose such as blocking the passage of tears or, with a passage through the plug, enhancing the passage of tears, or for a known medicating purpose such as supplying a medicament that is incorporated in the plug to the patient. According to the present invention, since each plug actually has two, or even more parts in some embodiments, and each can be loaded, using known technology, with a different medication, many more than four different medicaments can be supplied to one patient at the same time.

Each punctal plug arrangement 30 of the invention includes at least one anchor 32, and one plug 34. The anchor 32 and plug 34 are each advantageously made of any biocompatible material such as plastic, like silicone, or metal, like titanium, or metal impregnated plastic. It is also advantageous for either the anchor or the plug or both to be made of radio-opaque material or to be coated to be radio-opaque, so that the anchor and/or the plug are visible in an X-ray image.

Referring now to FIG. 2 in particular, the punctal plug arrangement 30 for placement in a lacrimal duct 20 of a patient, comprises the anchor 32 having an inner plug engaging recess 36 and an outer surface for engaging a wall of a lacrimal duct 20 for receiving the anchor. The plug 34 has a stem 38 for extending into the plug engaging recess 36 of the anchor 32. The plug 34 also has a head 40 connected to the stem 38, the head having a larger diameter then the stem for engaging around the lacrimal punctum 16 at an end of a lacrimal duct 18, 20, in which the anchor is received. The head 40 includes a tool engaging recess 42 for receiving the end 52 of a tool 50 for placing and for removing the plug and anchor, to be described later in this disclosure.

The anchor may have a radial skirt 44 to increase its fixation to the duct 20, and, according to the invention, anchor fixing means 46 at the outer surface of the anchor 32, such as a plurality of fixed or movable projections, provided for further fixing the anchor 32 to the wall of a lacrimal duct. The arrangement also includes plug fixing means such as a male thread on the stem 38 for treading into a female thread in the plug engaging recess 36, for detachable and axially securely connecting the plug 34 to the anchor 32, so that with the plug connected to the anchor, the plug and anchor can be inserted as a unit into, and removed as a unit from the lacrimal duct 20.

The arrangement of the invention includes the tool 50 having the end 52 for engaging the tool engaging recess 42 of the plug 34, the end of the tool and the tool engaging recess being shaped for axial securement of the tool to the plug so that the tool can be used to positively hold the plug, to facilitate insertion and removal of the plug and connected anchor into and out from the lacrimal duct.

In the embodiment of FIG. 2, this axial securement is achieved by making the tool engaging recess 42 of plug 34 larger at its base than at its entry end, and the end 52 of the tool to be radially expandable. Thus, with the tool end 52 in the tool engaging recess 42, end 52 is expanded in the larger base of the tool engaging recess 42 so that the tool is axially fixed to the plug. With the plug 34 also axially fixed to the anchor 32, e.g. by the threads, the plug plus the anchor, as a unit, can be securely held by the practitioner and inserted into the lacrimal duct through to punctum 16.

The radial expansion of tool end 52 can be provided by cutting a plurality of slots in the tool end 52 to form a plurality of prongs at the tool end, and by providing a central axial bore through the length of the tool 50. The bore has a constant diameter at the top of the tool, and becomes slightly smaller or tapers inwardly at 58, in the area of the tool end 52 and its slots and prongs. A cylindrical plunger 54 is slidably mounted into this cylindrical bore and has a top button end 56 that can be pressed by the practitioner. The lower end 60 of the plunger 54 stops just above the taper 58 in an initial condition of the tool 50, so that the prongs defined by the slots at the tool end 52, lay in the same plane as the six faces of the hexagonal tool body of tool 50. In this initial condition the tool end 52 can be inserted into the tool engaging recess 42 which is also hexagonal so that rotation of the tool 50 can be used to screw the plug stem into the anchor.

To axially secure the tool 50 to the plug 34, button 56 is pressed downwardly with respect to the tool body so that the plunger end 60 will slide along the inside tapered surfaces 58, and thereby cause the prongs to move radially outwardly into the enlarged base of tool receiving recess 42. In this engaged condition the plug plus anchor unit can be securely held and manipulated by the practitioner using the tool. The prongs are maintained in the expanded state due to friction between the plunger end 60 and the surfaces 58. Once the multi-part punctal plug 30 of the invention is in place, the practitioner will manually pull the plunger partly back out of the tool body to allow the prongs to spring back to their initial condition so that the tool end 52 can be released from the recess 42 and the plug 34.

The same procedure can be used to engage and extract the plug arrangement of the invention from the lacrimal duct.

Referring now to FIG. 4, the multi-part punctal plug arrangement of the invention comprises an anchor 32, plug 34 and tool 50, but has plug fixing means for connecting the plug to the anchor that comprises at least one, but preferably two, three or four radially movable latches 66 on the plug stem 38, and a latch seat 68 in the plug engaging recess 36 of the anchor, for detachably and axially securing the plug to the anchor.

The tool 50 includes latch retracting means for retracting the latch 66, radially inwardly to disengage the latch 66 from the latch seat 68 and disconnect the plug from the anchor. The anchor fixing means comprises a plurality of movable projections 47 on the outer surface of the anchor for engaging the wall of a lacrimal duct, the projections being radially movable and the tool including means for radially retracting the projections for facilitating removal of the anchor from the lacrimal duct.

The latch retracting means for retracting the latch 66, comprises an inner plunger 55 mounted for axial movement inside plunger 54 and having a lower end that engages the top of a pusher or push pin 70 mounted for axial movement inside plug 34, when the tool is engaged to the plug head 40. By pushing down on a second button 57 connected to the inner plunger 55, push pin 70 will push down on a spring 72 connected on the inner side of each latch 66, to pull the latch 66 radially inwardly, so it will clear latch seat 68 and allow the plug to be disconnected form the anchor. Since no rotational motion of the plug is needed, the body 51 of the tool 50 may be cylindrical rather than hexagonal and the tool engaging recess 43 is conical. Otherwise the tool end is expandable radially outwardly to engage the enlarged base of the tool engaging recess 43 by pushing down on button 56, as in the embodiment of FIG. 2.

The lower end of the push pin 70 will also transmit axial movement to a second spring 74, e.g. a V-shaped spring connecting the projections 47 in anchor 32, to pull the projections radially inwardly to disengage them from the walls of the lacrimal duct to allow the anchor to be pulled from the duct using the tool when the punctal plug arrangement is to be removed from the patient.

Medicament sacks 80 and 82 are also schematically shown FIG. 4, as examples of where and how medicaments can be charged into the punctal plug of the invention. The material of the anchor can be semipermeable to allow the medicine to be dosed to the patient, or one or more small channels can be provided in the anchor for this purpose, or another known manner of dosing the patient can be used.

As shown in FIG. 5, the multi-part punctal plug arrangement can build on the basic premise of the invention to provide more than two parts that can each be used for a different medicament in a single lacrimal duct. To this end the arrangement includes the anchor 32, the plug 34 and at least one, but two, three or even more, intermediate punctal sections 90, having an inner plug engaging recess 92 for receiving the stem 38 of plug 34, and an outer surface for engaging a wall of a lacrimal duct, the intermediate section 90 also having a stem 94 for extending into the plug engaging recess 36 of the anchor 32 so that the intermediate punctal section can be detachably and axially secured between the plug 34 and the anchor 32.

While specific embodiments of the invention have been shown and described in detail to illustrate the application of the principles of the invention, it will be understood that the invention may be embodied otherwise without departing from such principles.

What is claimed is:

1. A punctal plug arrangement comprising three separable parts for placement of an anchor and a plug in a lacrimal duct of a patient, the arrangement comprising:
   an anchor having an inner plug engaging recess and an outer surface for engaging a wall of a lacrimal duct for receiving the anchor;
   a plug having a stem for extending into and for removably engaging with the plug engaging recess of the anchor, and a head connected to the stem, the head having a larger diameter than the stem for engaging around a lacrimal punctum at an end of a lacrimal duct in which the anchor is received, the head including a tool engaging recess;
   wherein the plug engaging recess and the tool engaging recess are different recesses, and wherein said two recesses each comprise part of different physically separable components;
   an anchor fixing means at the outer surface of the anchor for fixing the anchor to the wall of a lacrimal duct for receiving the anchor;
   a plug fixing means for detachably and axially securely connecting the plug to the anchor so that with the plug connected to the anchor the plug and the anchor can be inserted as a unit into, and removed as a unit from, a lacrimal duct for receiving the anchor; and
   a tool having an end for removably engaging the tool engaging recess of the plug, the end of the tool and the tool engaging recess being adapted for axial securement of the tool to the plug so that the tool end can be used to selectably apply rotational, axial pushing, or axial pulling pressure on the plug;
   wherein the tool end and the tool engagement recess are adapted to facilitate insertion and removal of the plug and connected anchor into and out from a lacrimal duct for receiving the anchor;
   wherein the punctal plug arrangement is adapted so that, with the end of the tool engaged to the tool engagement recess, the tool can be used to detach the plug from the anchor, and also to apply axial pulling pressure to the plug, and thereby to remove the plug from a position engaged around a lacrimal punctum at the end of a lacrimal duct for receiving the anchor without also removing the anchor from a position within said same lacrimal duct;
   wherein the tool end is radially expandable;
   wherein the tool end comprises a plurality of prongs;
   wherein the tool comprises a bore throughout the length of the tool;
   wherein the bore tapers inwardly at the tool end;
   the tool further comprising a plunger shaped to fit within the bore and slidably positioned inside the bore;
   wherein a lower end of the plunger stops above the tapered portion of the bore in a first condition;
   wherein the prongs lay in substantially the same plane as the outside surface of the tool in the first condition;
   wherein the plunger may be pressed downwardly within the bore, with respect to the tool body, to achieve a second condition where the lower end of the plunger engages the tapered portion of the bore and causes the prongs to move radially outward at the tool end; and
   wherein the plunger may be moved upwardly within the bore, with respect to the tool body, to restore the tool to the first condition.

2. The punctal plug arrangement according to claim 1, wherein the plug fixing means comprises the stem of the plug and the inner plug engaging recess of the anchor being threaded so that the plug can be rotated using the tool to be detachably and axially secured to the anchor.

3. The punctal plug arrangement according to claim 1, wherein the anchor fixing means comprises a plurality of fixed projections on the outer surface of the anchor for engaging the wall of a lacrimal duct.

4. The punctal plug arrangement according to claim 1, wherein the end of the tool is radially expandable.

5. The punctal plug arrangement according to claim 1, further including tool fixing means for detachably and axially securely connecting the tool to the plug, wherein the tool fixing means is capable of communicating axial pulling pressure from the tool to the plug.

6. The punctal plug arrangement according to claim 1, including tool fixing means for detachably and axially securely connecting the tool to the plug, the tool fixing means including the tool having an expandable end, and the tool engaging recess having an enlarged base for receiving the expanded end of the tool, to axially secure the tool end to the plug.

7. The punctal plug arrangement according to claim 1, wherein the anchor fixing means comprise a plurality of projections on the outer surface of the anchor for engaging the wall of a lacrimal duct, the projections being radially movable and the tool including means for radially retracting the projections for facilitating removal of the anchor from the lacrimal duct.

8. The punctal plug arrangement according to claim 1, wherein the plug stem comprises at least one radially movable latch;
   further comprising a latch seat in the plug engaging recess of the anchor for detachably and axially securing the plug to the anchor by engagement with the movable latch;
   wherein the tool comprises latch retracting means for retracting the latch radially to disengage the latch from the latch seat and disconnect the plug from the anchor; and
   wherein the tool and the retractable latch are separable objects, and wherein the tool can be selectably removed from the punctal plug arrangement.

9. The punctal plug arrangement according to claim 1, further comprising a medicament in at least one of the plug and the anchor.

10. The punctal plug arrangement according to claim 1, wherein the plug and the anchor are adapted for insertion into the punctum as solid objects; and
   wherein at least one of the plug and the anchor are at least partly radio-opaque.

11. The punctal plug arrangement according to claim 1, further comprising a second plunger mounted for axial movement within the first plunger;

wherein the plug stem comprises at least one radially movable latch;

the punctal plug arrangement further comprising a latch seat in the plug engaging recess of the anchor for detachably and axially securing the plug to the anchor by engagement with the movable latch;

wherein the second plunger is adapted to selectably pull the movable latch radially inward to disengage the latch from the latch seat and thereby disconnect the plug from the anchor; and wherein the tool and the retractable latch are separable objects.

* * * * *